(12) United States Patent
Wilson et al.

(10) Patent No.: US 12,030,022 B2
(45) Date of Patent: Jul. 9, 2024

(54) MULTILAYERED WIRE MESH-SUPPORTED MEMBRANES FOR SEPARATION APPLICATIONS

(71) Applicant: Engi-Mat Co., Lexington, KY (US)

(72) Inventors: David Wilson, Lexington, KY (US); Haibing Wang, Phoenix, AZ (US); Claudia Goggin, Lexington, KY (US); Brian Mackey, Lexington, KY (US)

(73) Assignee: Engi-Mat Co., Lexington, KY (US)

( * ) Notice: Subject to any disclaimer, the term of this patent is extended or adjusted under 35 U.S.C. 154(b) by 0 days.

(21) Appl. No.: 18/183,255

(22) Filed: Mar. 14, 2023

(65) Prior Publication Data

US 2023/0294047 A1    Sep. 21, 2023

Related U.S. Application Data

(60) Provisional application No. 63/320,308, filed on Mar. 16, 2022.

(51) Int. Cl.
*B01D 69/10* (2006.01)
*B01D 61/36* (2006.01)
(Continued)

(52) U.S. Cl.
CPC ......... *B01D 69/108* (2022.08); *B01D 61/362* (2013.01); *B01D 61/363* (2022.08);
(Continued)

(58) Field of Classification Search
None
See application file for complete search history.

(56) References Cited

U.S. PATENT DOCUMENTS 5,069,791 A * 12/1991 Becker ............... B01D 25/28
210/409
5,376,442 A    12/1994 Davidson et al.
(Continued)

FOREIGN PATENT DOCUMENTS

DE    19905638 C1 *  6/2000  ......... B01D 39/2027
EP    3 928 858 A1    12/2021
(Continued)

OTHER PUBLICATIONS

Picksley et al, "Characteristics of filter aids", Brewing research foundation, Aug. 1988 (Year: 1988).*
(Continued)

*Primary Examiner* — Krishnan S Menon
(74) *Attorney, Agent, or Firm* — Bell & Manning, LLC

(57) ABSTRACT

Composite structures composed of inorganic membranes or polymer membranes supported on a multilayered woven wire mesh substrate are provided. Also provided are methods of making the composite structures and methods of using the composite structures as separation membranes. The mesh substrates are composed of a stack of two or more layers of woven wire mesh, wherein the different mesh layers in the stack have different mesh sizes. The multilayered mesh structure can support a defect-free, or substantially defect-free, membrane and has sufficient mechanical strength to allow the supported membranes to be used for chemical separations.

22 Claims, 4 Drawing Sheets

(51) Int. Cl.
*B01D 67/00* (2006.01)
*B01D 69/04* (2006.01)
*B01D 71/02* (2006.01)
*C02F 1/44* (2023.01)
*C02F 101/34* (2006.01)
*C07C 29/86* (2006.01)

(52) U.S. Cl.
CPC ......... *B01D 67/0039* (2013.01); *B01D 69/04* (2013.01); *B01D 71/0281* (2022.08); *C02F 1/448* (2013.01); *C07C 29/86* (2013.01); *C02F 2101/34* (2013.01)

(56) References Cited

U.S. PATENT DOCUMENTS

| | | | |
|---|---|---|---|
| 5,468,699 | A | 11/1995 | Zhang et al. |
| 9,457,340 | B2 | 10/2016 | Buelow et al. |
| 2002/0041837 | A1 | 4/2002 | Edlund et al. |
| 2008/0149561 | A1* | 6/2008 | Chu ............... D01D 5/0084 264/165 |
| 2009/0000475 | A1 | 1/2009 | Fekety et al. |
| 2010/0304953 | A1 | 12/2010 | Liu et al. |
| 2011/0052466 | A1 | 3/2011 | Liu |
| 2012/0152843 | A1 | 6/2012 | McEvoy et al. |
| 2014/0223873 | A1* | 8/2014 | Ebrahimi Warkiani ............... B01D 39/083 210/488 |
| 2014/0319706 | A1 | 10/2014 | Huizing et al. |
| 2016/0200282 | A1 | 7/2016 | Lowe |
| 2018/0339271 | A1 | 11/2018 | Dubois et al. |
| 2019/0176097 | A1 | 6/2019 | Liu |
| 2021/0131753 | A1* | 5/2021 | Yang ............... F28F 13/185 |

FOREIGN PATENT DOCUMENTS

| | | |
|---|---|---|
| WO | 2011062998 A2 | 5/2011 |
| WO | 2011159389 A1 | 12/2011 |

OTHER PUBLICATIONS

Mahmodi, Ghader, et al. "NaA zeolite-coated meshes with tunable hydrophilicity for oil-water separation." Separation and Purification Technology 240 (2020): 116630.

Zhang, Jian, and Wei Liu. "Thin porous metal sheet-supported NaA zeolite membrane for water/ethanol separation." Journal of Membrane Science 371.1-2 (2011): 197-210.

Gao, Liyue, et al. "Preparation of a novel zeolite Y-stainless-steel wire mesh honeycomb for VOC capture." Microporous and Mesoporous Materials 328 (2021): 111438.

Makertihartha, I. G. B. N., P. T. Dharmawijaya, and I. G. Wenten. "Recent advances on bioethanol dehydration using zeolite membrane." Journal of Physics: Conference Series. vol. 877. No. 1. IOP Publishing, 2017.

The International Search Report and the Written Opinion issued on Jul. 12, 2023 for international patent application No. PCT/US2023/064275; pp. 1-8.

The International Search Report and Written Opinion issued for international patent application No. PCT/US2023/064275 on Jul. 12, 2023; pp. 1-8.

* cited by examiner

MULTILAYERED WIRE MESH-SUPPORTED MEMBRANES FOR SEPARATION APPLICATIONS

CROSS REFERENCE TO RELATED APPLICATIONS

The present application claims priority to U.S. provisional patent application No. 63/320,308 that was filed Mar. 16, 2022, the entire contents of which are incorporated herein by reference.

REFERENCE TO GOVERNMENT RIGHTS

This invention was made with government support under DE-SC0017141 awarded by the Department of Energy. The government has certain rights in the invention.

BACKGROUND

Many bioethanol plants in the U.S. run an energy-intensive pressure swing adsorption (PSA) process for the dehydration of organic solvents. However, PSA requires periodic adsorbent bed retrofitting, which is time-consuming and expensive. Emerging energy-efficient separation technologies such as membranes also can be used for ethanol dehydration. NaA zeolite membranes, in particular, are highly effective for the dehydration of various organic solvents due to their hydrophilic properties and molecular sieving effect. During operation, zeolite membrane systems do not require recycling. As a result, bioethanol manufacturers are able to reduce energy costs and increase production capacity by replacing PSA processes with zeolite membrane dehydration systems or by integrating zeolite membrane modules into their existing processes. Unfortunately, the production costs of NaA zeolite membranes are high, with most of the costs coming from the porous ceramic or metallic supports.

SUMMARY

Supported membranes, methods of making the supported membranes, and methods of using the supported membranes in the separation of chemical species are provided.

One embodiment of a supported membrane includes: (a) a multilayered mesh substrate comprising: (i) a first layer comprising a first woven wire mesh having an absolute micron rating of 15 μm or smaller; and (ii) a second layer underlying the first layer, the second layer comprising a second woven wire mesh having an absolute micron rating larger than the absolute micron rating of the first woven wire mesh; and (b) a continuous porous membrane on the first woven wire mesh.

One embodiment of a method of making a supported membrane includes the steps of: (a) providing a multilayered mesh substrate comprising: (i) a first layer comprising a first woven wire mesh having an absolute micron rating of 15 μm or smaller; and (ii) a second layer underlying the first layer, the second layer comprising a second woven wire mesh having an absolute micron rating larger than the absolute micron rating of the first woven wire mesh; and (b) forming a continuous porous membrane on a surface of the first woven wire mesh, opposite the second layer of woven metal wire mesh.

One embodiment of a method for separating molecules from a feed mixture comprising a first molecule and a second molecule having a larger molecular size than the first molecule utilizes a supported membrane comprising: (a) a multilayered mesh substrate comprising: a first layer comprising a first woven wire mesh having an absolute micron rating of 15 μm or smaller; and a second layer underlying the first layer, the second layer comprising a second woven wire mesh having an absolute micron rating larger than the absolute micron rating of the first woven wire mesh; and (b) a continuous porous membrane on the first woven wire mesh. The method includes the steps of: exposing the feed mixture to a first surface of a supported membrane comprising; and creating a pressure difference between the first surface of the supported membrane and an opposing surface of the supported membrane, wherein the pressure at the first surface is greater than the pressure at the opposing surface, or vice versa, and the first molecule is selectively removed from the feed mixture by the continuous porous membrane.

BRIEF DESCRIPTION OF THE DRAWINGS

Illustrative embodiments of the invention will hereafter be described with reference to the accompanying drawings, wherein like numerals denote like elements.

DETAILED DESCRIPTION

Composite structures comprising inorganic membranes or organic membranes supported on multilayered woven mesh supports are provided. Also provided are methods of making the composite structures and methods of using the composite structures in chemical separations.

The composite structures use readily available inexpensive woven wire meshes as a starting material for the fabrication of supported membrane structures. By using low-cost meshes as porous supports, supported membrane structures can be synthesized in an economical way for a wide range of applications, including energy-efficient bioethanol dehydration and gas-phase separations.

The meshes used as porous supports are composed of stacks of two or more layers of woven wire mesh, wherein the different mesh layers in the stack have different mesh sizes. The multilayered mesh structure is able to support a defect-free, or substantially defect-free, membrane and has sufficient mechanical strength to allow the supported membranes to be used for chemical separations in a planar geometry.

Figure 1:
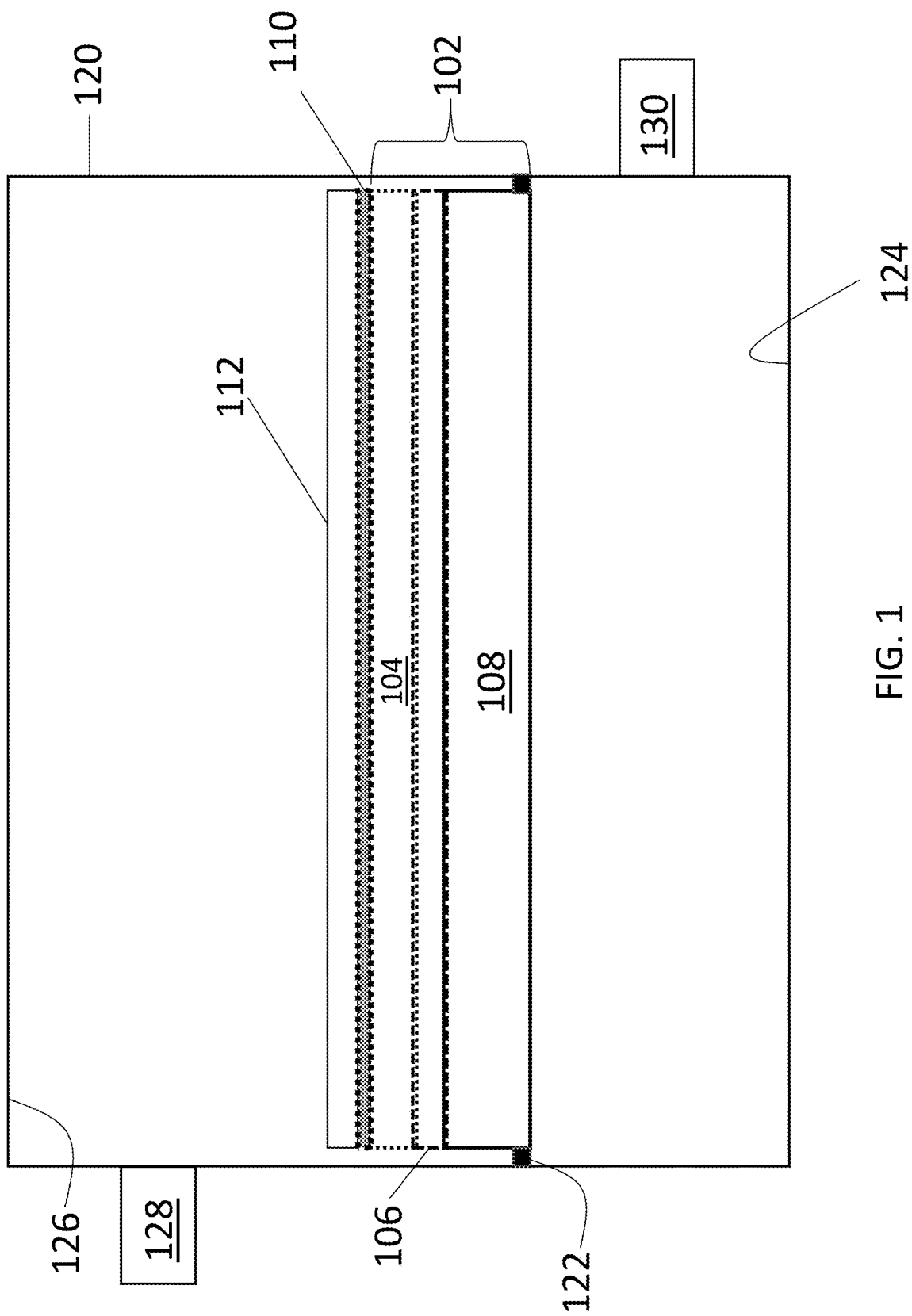
FIG. 1 is a schematic diagram of a supported membrane structure that includes a triple layer mesh stack, a ceramic coating on the upper surface of the mesh stack, and a porous membrane over the ceramic coating.

One example of a composite structure based on a multilayered woven mesh stack is shown schematically in FIG. 1. From top to bottom, the multilayered mesh stack 102 includes a first layer comprising a first woven wire mesh 104, a second woven wire mesh 106, and a third woven wire mesh 108. For purposes of illustration this exemplary composite structure uses a triple-layer mesh stack. However, if should be understood that a mesh stack having only two wire mesh layers, or a mesh stack having four or more mesh layers can also be used. The surface of first woven wire mesh 104 opposite second woven wire mesh 106 is coated with a ceramic 110 and a membrane 112 is disposed on the ceramic coated wire mesh 110/104. The mesh layers in multilayered mesh stack 102 are desirably sintered in order to form strong bonds between the wires and between mesh layers through heat and, optionally, pressure. The thickness of each layer 104, 106, 108 of multilayered mesh stack 102 will be determined by the gauge (diameter) of the wire used for the mesh of that layer. While each layer of mesh 104, 106, 108 can be a single mesh sheet, it is also possible to use multiple (i.e., two or more) mesh sheets in one of more of the layers.

First woven wire mesh 104 has the highest mesh count and the smallest pore size (i.e., the smallest mesh openings), where mesh count refers to the number of openings in the mesh per linear inch. This mesh desirably has an absolute micron rating of 15 μm or smaller and more desirably 10 μm or smaller, where the absolute micron rating corresponds to the diameter of the largest spherical glass particle that can pass through the openings in the mesh. High mesh count woven wire meshes can be provided by, for example, a tightly woven off-count mesh. By way of illustration, woven wire meshes having a mesh count of 200×1400 or higher, including 325×2300 or higher, and a high-count weave, such as a twill Dutch weave, can be used.

For some applications, even such low micron rating meshes have pore sizes that are too large to render them practical for use as membrane supports. Moreover, for membranes made via seeding, even the low-micron rating woven wire meshes may have openings that are too large for optimal seeding. In such instances, ceramic coating 110 can be used to reduce the opening sizes in first woven wire mesh 104, as discussed in more detail below.

Second woven wire mesh 106 is of an intermediate mesh count and pore size. When present, this mesh provides additional mechanical support for the composite supported membrane structure, provides a more strongly bonded sintered mesh structure than would be produced in the absence of this intermediate mesh layer, and/or results in a smoother first woven wire mesh 104 after sintering and pressing than would result in the absence of this intermediate mesh layer. The mesh count of second woven wire mesh 106 is smaller than that of first woven wire mesh 104, but is otherwise not particularly limited. Thus, by way of illustration, woven wire meshes having an absolute micron rating of 50 μm or greater, including 100 μm or greater, may be used. Intermediate mesh count woven wire meshes can be provided by, for example, an intermediate weave off-count woven mesh or an intermediate weave mesh having the same mesh count in both directions. By way of illustration, woven wire meshes having a mesh count in the range from 80×80 to 120×120 can be used. The intermediate mesh count weave may be provided, for example, by a straight weave or a plain Dutch weave. However, second woven wire mesh 106 can have a mesh count outside of the above-cited range and/or may have a different weave type.

Third woven wire mesh 108 is used primarily for mechanical support and, therefore, may be formed from an inexpensive, low mesh count woven wire mesh having openings that would render the mesh impractical or unsuitable for use by itself as a support for some membrane-based applications, such as chemical separation applications. Examples of woven wire meshes that are suitable for use as third woven wire mesh 108 include square (straight) weave meshes having a mesh count of 60×60 or lower, which are readily commercially available and generally cost less than higher count meshes.

The wire meshes may be metal wire meshes, but may also be meshes made from other materials, such as ceramics. Moreover, in a mesh stack one or more wire meshes may be metal meshes, while one or more other wire meshes may be composed of another material, such as a ceramic. Metals from which the meshes can be made include single element metals and metal alloys. The metal can be selected based on the intended application of the composite structures. However, for applications in which the multilayered mesh is acting only as a passive support structure, cost and availability may be important factors. Examples of metal meshes that can be used include, but are not limited to, stainless steel, non-stainless steel, nickel (Ni), chromium-nickel, and copper (Cu) wire meshes. Examples of ceramic meshes include silicon carbide meshes. It should be understood that, for the purposes of this disclosure, the term "wire" refers to metal wires in the case of woven metal wire meshes, but also refers to the ceramic strands in the case of woven ceramic wire meshes.

Ceramic coating 110 is an optional coating applied over first woven mesh 104 in order to provide thermal stability and prevent cracking of overlying membrane 112, due to any difference in the coefficients of thermal expansion of mesh layer 104 and membrane 112. In addition, as described above, ceramic coating 110 can be used to completely or partially fill the openings in first woven wire mesh 104, or even to completely cover first woven wire mesh 104, in order to provide a smoother surface and/or to improve seeding of the growth of membrane 112. Ceramic coating 110 may be formed in situ by applying a ceramic powder onto the top surface of the first woven wire mesh 104 and sintering the mesh and the powder to form a ceramic coating. The ceramic coating may then be polished to provide a smoother surface. Ceramic coating 110 is a porous structure, typically having pores sizes of about 50 nm or larger.

The particular ceramic used for ceramic coating 110 should have a coefficient of thermal expansion that is intermediate between the coefficients of thermal expansion of mesh layer 104 and membrane 112. Therefore, the selection of the ceramic will depend on the material of first woven wire mesh 104 and the composition of membrane 112. Alumina, silicon carbide, and tungsten carbide are examples of ceramics that can provide thermal stability between a zeolite membrane and a stainless-steel mesh, as well as other membrane/mesh combinations.

It should be noted that, while FIG. 1 depicts a composite structure that includes a ceramic coating between the mesh and the membrane and much of the discussion herein focuses on composite structures that include the ceramic coating, some embodiments of the composite structure can omit the ceramic coating. For example, if the coefficients of thermal expansion for the material of the mesh and the particular membrane being used are similar or if the particular application does not require a high-quality (e.g., crack-free) membrane, the ceramic layer 110 may be omitted.

Optionally, if a ceramic coating 110 is not formed on first woven mesh 104, but smaller openings are desirable for subsequent membrane seeding, filler particles can be applied onto first woven wire mesh 104, the function of which is to provide a smoother surface and reduce the pore size and pore volume of the mesh. The filler particles may be ceramic particles that are left un-sintered and, therefore, do not form a coating. However, non-ceramic particles can also be used.

Membrane 112 is a porous structure and may be an inorganic membrane or an organic membrane. Depending upon whether membrane 112 of the composite structure is an inorganic membrane, such as a zeolite membrane, or an organic membrane, such as a polymeric membrane, the ceramic-coated surface of first woven wire mesh 110/104 (or simply first woven wire mesh 104 if no ceramic coating is present) is seeded with membrane seed particles or inorganic filler particles.

As used herein, the term "membrane seed particles" refers to particles from which a continuous membrane is grown or formed in a subsequent processing step. The membrane seed particles may have the same chemical composition as the membrane itself or may have a different chemical composition than the membrane. Examples of membrane seed particles for the fabrication of inorganic membranes include zeolite particles and other ceramic particles. Ceramics include various inorganic compounds of metals, metalloids, and non-metals, including oxides, nitrides, and oxynitrides. Zeolites are crystalline porous aluminosilicates of sodium, potassium, calcium, and/or barium that have a wide range of applications in chemical separations and catalysis. For example, zeolite-NaA is a sodium aluminosilicate zeolite with highly hydrophilic properties and nanopores with diameters of less than 1 nm (approximately 0.3 nm to 0.5 nm) that is used as a catalyst and adsorbent in a variety of chemical processes, including the selective removal of water from organic solutions. The ceramic from which the membranes are composed may differ from the ceramic of the thermally-stabilizing ceramic coating and the ceramic membrane will have a smaller average pore size than the ceramic coating. However, it is also possible to use the same material for ceramic coating 110 and membrane 112, wherein membrane 112 is denser and has a smaller average pore size than ceramic coating 110.

Seeding can be carried out by preparing a suspension of membrane seed particles and/or filler particles and infusing the suspension into the pores of the ceramic-coated first woven wire mesh by, for example, immersing the ceramic-coated mesh in the suspension to embed the membrane seed particles and/or filler particles in the structure. The ceramic-coated woven wire mesh can then be dried to remove the volatile components of the suspension, such as water and/or organic solvents. The membrane seed particle loading should be sufficient to fabricate a continuous membrane that covers the openings in the underlying woven wire mesh. It should be understood that the membrane is continuous in the sense that it spans and covers the openings in the underlying woven wire mesh (see, for example, FIG. 4); however, the membrane is also porous on a very small scale, having pore sizes on the micro-scale, nano-scale, or smaller (e.g., 1 μm or smaller; 100 nm or smaller). For example, the membrane may be microporous, having pore sizes of 2 nm or smaller. Thus, while a continuous membrane may have very small pores, those pores do not correspond in size, shape, or location with the openings in the underlying mesh.

The membrane seed particles may be used to form an inorganic membrane in situ on the ceramic-coated woven wire mesh support via hydrothermal synthesis, which converts the seed particles into a membrane. In hydrothermal synthesis, the seeded, ceramic-coated multilayered mesh support is exposed to a solution, such as an aqueous solution or gel, that includes chemical elements, molecules, and/or compounds containing the constituents of the membrane to be formed. These chemical elements, molecules, and/or compounds are referred to as membrane precursors. By way of illustration, the membrane precursors for a zeolite membrane would include aluminum- and silicon-containing elements, molecules, and/or compounds. Specific examples of membrane precursors that can be used to form a NaA zeolite membrane include sodium hydroxide, sodium metasilicate nonahydrate, and sodium aluminate. Optionally, additional components, such as mineralizing agents and/or structure-directing agents, can be included in the solution. Under hydrothermal conditions at elevated temperatures, the membrane precursors nucleate into crystals on the seed particles and grow into a continuous membrane. Hydrothermal membrane synthesis is generally carried out at elevated temperatures for a duration of hours or days. By way of illustration, hydrothermal zeolite membrane synthesis may be carried out at temperatures in the range from about 50° C. to about 250° C. for a period of about 5 hours to about 72 hours. However, temperatures and time periods outside of these ranges can be used. The resulting membrane may cover the entire exposed surface of the first woven wire mesh, or only a portion thereof. Because the membrane is grown from seed particles located within the pores of the woven wire mesh, the membrane extends into and is integrated with the mesh structure.

If the membrane to be formed is an organic polymer membrane, the particles seeded into the ceramic coated mesh structure need not be membrane seed particles. Instead, ceramic filler particles can be used, the function of which is to reduce the pore volume in the mesh and, if present, the ceramic coating, and provide a substrate onto which a polymer coating can be applied in a subsequent processing step. The polymer membrane can be applied over the ceramic filler particles as a fully-polymerized polymer, or may be applied as polymer precursors that are subsequently polymerized and/or crosslinked into a polymer membrane. The polymer precursors are organic molecules, such as monomers, oligomers, crosslinking agents, and/or resins, that include the constituents of the polymer to be formed.

The multilayered meshes and the composite structures made therefrom may have a square or rectangular perimeter, or may have other perimeter shapes, including circular. Moreover, although the multilayered mesh supports and the supported membranes formed from the multilayered meshes can have a substantially planar configuration, they can also have more complex non-planar configurations. For example, the supported membranes can be formed into a hollow cylinder by, for example, rolling a planar supported membrane into a hollow tube and connecting the edges to seal the cylinder.

One or more of the composite structures may be provided in a housing 120 to form a module. Within the housing, the composite structures may be arranged in a vertical stack and/or side-by-side. The housing may include, for example, a frame 122 disposed around the perimeters of the one or more composite structures and the one or more composite structures may be attached to the frame. The housing may also include a lower support (e.g., a floor) 124 upon which the one or more composite structures rests, or over which the one or more composite structures is supported, and may also include a cover 126 over the one or more composite structures. Conduits 128, 130 for introducing a fluid (e.g., a gas or liquid) into and out of the housing may be formed in the housing to allow for the fluid to pass through the one or more composite structures and then out of the housing.

While the composite structures made according to the methods described herein can be designed for many applications, depending on the nature of the membranes, the structures having integrated hydrophilic zeolite membranes, such as NaA zeolite membranes, are particularly well-suited for use for in separating chemicals, such as separating water from fluid mixtures in a dehydration. In a dehydration, water can be separated from one or more other components in a mixture based on differences in the molecular size of those components and water. The separations are carried out by passing the mixture through one or more of the composite structures, whereby the membrane preferentially passes the water molecules, while preferentially capturing the other component or components. For the purposes of this disclosure a molecule is preferentially passed if it passes through the membrane more readily than do other molecules from which it is being separated. Similarly, a molecule is preferentially captured if it is retained by the membrane more readily than other molecules from which it is being separated. Examples of components that can be separated from water in a dehydration include oils and organic solvents. By way of illustration, the composite structures can be used in the pervaporation or vapor permeation of water from a feed stream comprising a mixture of water and one or more organic liquids, such as alcohols, esters, and the like. In the pervaporation and vapor permeation processes, the hydrophilic zeolite membrane enhances the permeation and evaporation of water from the mixture through the membrane under the influence of a pressure difference across the membrane. Pervaporation is a method for the separation of mixtures of liquids by partial vaporization through a nonporous or porous membrane. Alcohols that can be dehydrated using the composite structures include, but are not limited to, ethanol and isopropanol.

The composite structures made according to the methods described herein can be designed for use in gas-phase separations. For example, the composite structures can be used to separate small gas-phase molecules, such as $H_{2(g)}$, $O_{2(g)}$, $N_{2(g)}$, or a mixture of two or three thereof, from larger molecules in a gas stream via selective permeation (i.e., size exclusion of the larger molecules/size inclusion of smaller molecules) through the composite structure. Composite structures having porous polymer or zeolite membranes may be used for such separations. Examples of components that can be separated from organic molecules, such as alkanes, via size inclusion include $H_{2(g)}$, $O_{2(g)}$, and/or $N_{2(g)}$. By way of illustration, the composite structures can be used to separate $H_{2(g)}$, $O_{2(g)}$, and/or $N_{2(g)}$ from natural gas. Suitable polymers for the membranes include polyimides. Suitable zeolites for the membranes include MFI, LTA, MOR, and FAU type membranes.

EXAMPLE

This example describes the fabrication of a zeolite membrane supported on a multilayered mesh support comprising three layers of woven stainless steel wire mesh.

For the top layer to the bottom layer, the structure had the following architecture: NaA zeolite membrane; ceramic intermediate layer (coating); and triple-layer stainless steel mesh. The resulting structure, made according to the methods described below, had a defect-free NaA zeolite membrane.

Multilayered Woven Stainless-Steel Wire Mesh

Figure 2:
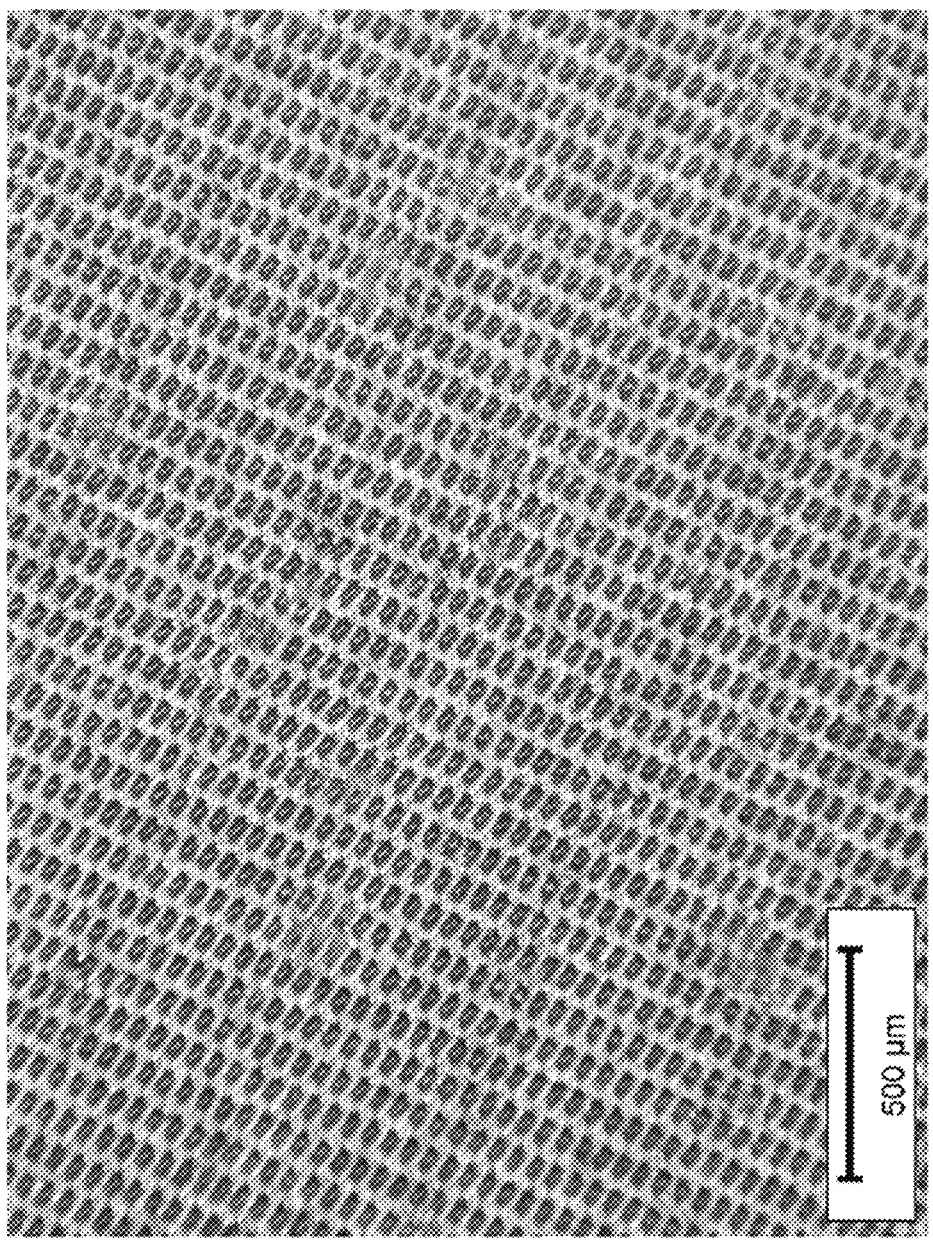
FIG. 2 is an image of the top surface of the first (top) layer of the triple layer stainless steel mesh structure used in the Example.

The triple-layer stainless steel (SS316L) mesh was a sintered mesh purchased as a special order from Lawrence Sintered Metals, Inc. The three layers in the mesh from top to bottom were as follows: first woven stainless steel wire mesh=325×2300 Mesh, Twilled Dutch Weave (absolute micron rating=8 μm; nominal micron rating=2 μm); second woven stainless steel wire mesh=100×100 Mesh, Straight Woven Wire Weave; and third woven stainless steel wire mesh=50×50 Mesh, Straight Woven Wire Weave. An image of the upper surface of the first woven stainless steel wire mesh is shown in FIG. 2.

Ceramic Coating

Figure 3:
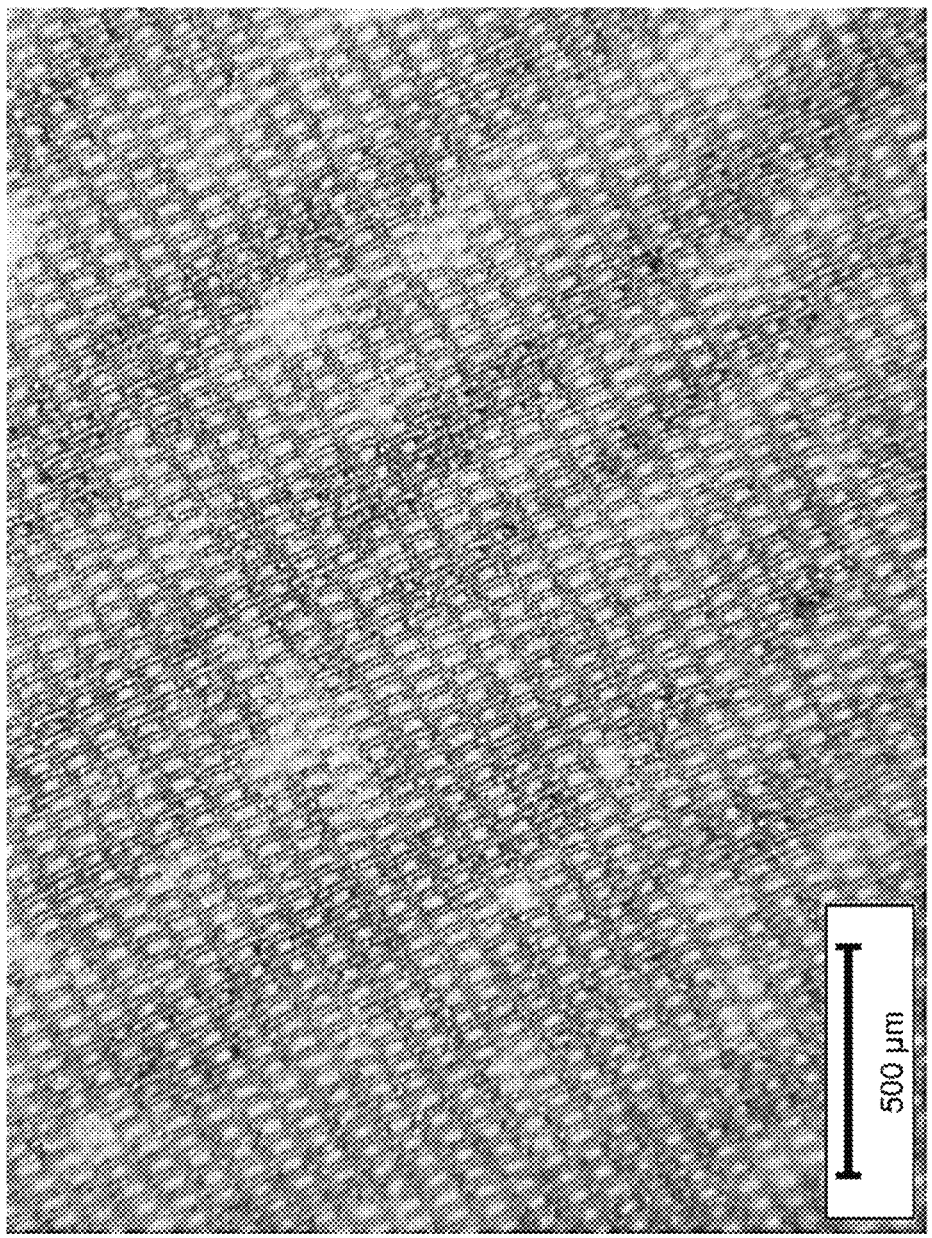
FIG. 3 is an image of the top surface of the triple layer stainless steel mesh used in the Example after coating with alumina and polishing.

To enhance thermal stability and smooth the surface of the structure, a ceramic intermediate layer was applied to the three-layer stainless steel mesh stack. The ceramic layer addresses the risk of cracking due to the differences in coefficients of thermal expansion of the NaA zeolite and the stainless steel and prepares the structure for the seeding of the NaA membrane. To form the ceramic interlayer, powdered alumina was applied to the surface of the 325×2300 mesh layer. The ceramic particles and stainless-steel mesh were then subjected to a sintering procedure. The sintering process was carried out under forming gas (5% hydrogen, balance argon) with a heating rate of 2 degrees per minute to 300° C., which was held for 8 hours, followed by a heating to 1225° C. at 2 degrees per minute for 6 hours. The furnace was then cooled down to room temperature at 2 degrees per minute. After sintering, the surface of the ceramic-coated mesh was polished with sandpaper. An image of the polished surface is shown in FIG. 3.

NaA Zeolite Membrane

Once the hybrid, metal-ceramic support structure was prepared, an NaA zeolite membrane was fabricated over the alumina-coated stainless-steel mesh. To grow a uniform and defect free NaA zeolite membrane, the surface of the ceramic-coated top stainless-steel mesh was seeded with an NaA powder that was prepared by milling a commercially available NaA zeolite powder.

The commercially purchased zeolite was rated 325 mesh so the particle size was less than 44 microns. The as-purchased zeolite was ball milled to decrease the average particle size and make the particles smaller and more uniform.

Figure 4:
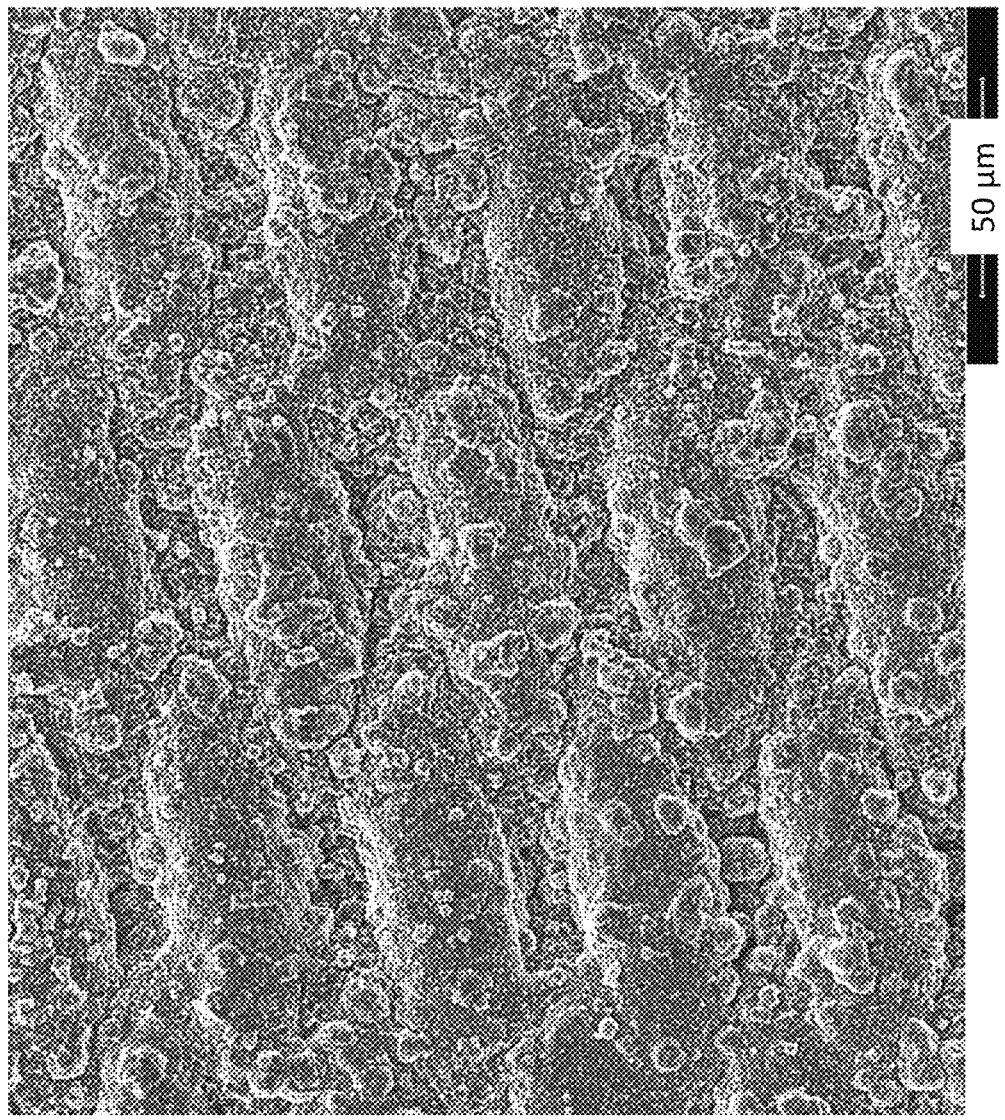
FIG. 4 is an image of the top surface of a continuous NaA membrane on the alumina-coated triple layer stainless steel mesh structure used in the Example.

After seed powder application, a continuous NaA zeolite membrane was synthesized on the surface of the alumina-coated 325×2300 Mesh using hydrothermal growth. An image of the continuous NaA membrane on the alumina-coated stainless-steel mesh is shown in FIG. 4. The patterned ridges visible in the picture are indicative of underlying wires of the mesh layer. However, as can be seen in the image, the pores defined by the wires are covered by the continuous membrane.

The hydrothermal growth process used a process published in the literature for growing NaA zeolites with only minor variations. (See, Zhang, Jim, and Wei Liu. "Thin porous metal sheet-supported NaA zeolite membrane for water/ethanol separation." *Journal of Membrane Science* 371.1-2 (2011): 197-210.) The synthesis solution 2 had a composition of $6.8Na:2Si:2Al:155H_2O$. It was prepared by the following procedure: 1.46 g sodium hydroxide (Sigma-Aldrich, 99.99%) was dissolved in 123 g $H_2O$ by stirring for 5 min; 9.93 g sodium aluminate (Spectrum) was added and stirred for 3 h; finally, 11 g sodium metasilicate (Aldrich, $SiO_2$ 44-47%) was added and stirred vigorously for 30 min to obtain a homogeneous solution. The seeded porous metal substrates were used for membrane growth in the synthesis. For each growth experiment, 18 ml of the synthesis solution was poured into a 23 ml autoclave reactor. The reactor was sealed and the hydrothermal growth was conducted at 80° C. for various times. After hydrothermal growth, the membrane was rinsed under running de-ionized water and dried in compressed air at room temperature.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" can mean only one or can mean "one or more". Embodiments of the inventions consistent with either construction are covered.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A supported membrane comprising:
   (a) a multilayered mesh substrate comprising:
   a first layer comprising a first woven wire mesh having an absolute micron rating of 15 µm or smaller; and
   a second layer underlying and adjacent to the first layer, the second layer comprising a second woven wire mesh having an absolute micron rating larger than the absolute micron rating of the first woven wire mesh;
   (b) a continuous porous membrane over a top surface of the first woven wire mesh, wherein the continuous porous membrane spans and covers mesh openings in the top surface of the first woven wire mesh; and
   (c) optionally, a ceramic coating on the top surface of the first woven wire mesh underlying the continuous porous membrane.

2. The supported membrane of claim 1, wherein the first woven wire mesh and the second woven wire mesh are metal wire meshes.

3. The supported membrane of claim 1, wherein the multilayered mesh substrate further comprises at least one additional layer underlying the second layer, the at least one additional layer comprising an additional woven wire mesh having an absolute micron rating larger than the absolute micron rating of the second woven wire mesh.

4. The supported membrane of claim 3, wherein the additional woven wire mesh is a metal wire mesh.

5. The supported membrane of claim 1, wherein the first and second woven wire meshes are stainless steel meshes.

6. The supported membrane of claim 1, comprising the ceramic coating on the top surface of the first woven wire mesh, underlying the membrane.

7. The supported membrane of claim 1, wherein the membrane comprises a zeolite.

8. The supported membrane of claim 6, wherein the ceramic of the ceramic coating has a coefficient of thermal expansion that lies between the coefficients of thermal expansion of the first woven wire mesh and the membrane.

9. The supported membrane of claim 1, wherein the supported membrane is in the form of a hollow cylinder.

10. A method of making a supported membrane, the method comprising:
    providing a multilayered mesh substrate comprising:
    a first layer comprising a first woven wire mesh having an absolute micron rating of 15 µm or smaller; and
    a second layer underlying and adjacent to the first layer, the second layer comprising a second woven wire mesh having an absolute micron rating larger than the absolute micron rating of the first woven wire mesh; and
    forming a continuous porous membrane over a top surface of the first woven wire mesh, opposite the second layer of woven metal wire mesh, wherein the continuous porous membrane spans and covers mesh openings in the top surface of the first woven wire mesh; and
    optionally, forming a ceramic coating on the top surface of the first woven wire mesh, prior to forming the continuous porous membrane.

11. The method of claim 10, wherein the first woven wire mesh and the second woven wire mesh are metal wire meshes.

12. The method of claim 10, wherein the multilayered mesh substrate further comprises at least one additional layer underlying the second layer, the at least one additional layer comprising an additional woven wire mesh having an absolute micron rating larger than the absolute micron rating of the second woven wire mesh.

13. The method of claim 12, wherein the additional woven wire mesh is a metal wire mesh.

14. The method of claim 10, comprising forming the ceramic coating on the surface of the first woven wire mesh, prior to forming the continuous porous membrane.

15. The method of claim 10, wherein the membrane comprises a zeolite.

16. A method for separating molecules from a feed mixture comprising a first molecule and a second molecule having a larger molecular size than the first molecule, the method comprising:
    exposing the feed mixture to a first surface of a supported membrane comprising:
    (a) a multilayered mesh substrate comprising:
    a first layer comprising a first woven wire mesh having an absolute micron rating of 15 µm or smaller; and
    a second layer underlying the first layer, the second layer comprising a second woven wire mesh having an absolute micron rating larger than the absolute micron rating of the first woven wire mesh;
    (b) a continuous porous membrane over a top surface of the first woven wire mesh, wherein the continuous porous membrane spans and covers mesh openings in the top surface of the first woven wire mesh; and
    (c) optionally, a ceramic coating on the top surface of the first woven wire mesh underlying the continuous porous membrane; and
    creating a pressure difference between the first surface of the supported membrane and an opposing surface of the supported membrane, wherein the pressure at the first surface is greater than the pressure at the opposing surface, or vice versa, and the first molecule is removed from the feed mixture by the continuous porous membrane.

17. The method of claim 16, wherein the first molecule is liquid water and the water is removed from the feed mixture via pervaporation or preferential vapor permeation through the continuous porous membrane.

18. The method of claim 17, wherein the molecule having a larger molecular size than water is an organic molecule.

19. The method of claim 16, wherein the continuous porous membrane comprises a zeolite.

20. The method of claim 18, wherein the organic molecule comprises an alcohol.

21. The method of claim 16, wherein the first molecule comprises $H_{2(g)}$, $O_{2(g)}$, $N_{2(g)}$, or a mixture of two or three thereof.

22. The supported membrane of claim 1, wherein the continuous porous membrane comprises pores with pore sizes of 2 nm or smaller.

\* \* \* \* \*